United States Patent
Jeong et al.

(10) Patent No.: US 8,345,338 B2
(45) Date of Patent: Jan. 1, 2013

(54) METHOD OF MODIFYING COLOR COMPOSITION FOR A COLOR-BLIND PERSON IN A MOBILE DISPLAYING APPARATUS

(75) Inventors: Young-Min Jeong, Suwon-si (KR); Seok-Jin Won, Seongnam-si (KR); Sung-Dae Cho, Yongin-si (KR); Sang-Wook Oh, Ansan-si (KR); Kyoung-Ju Park, Seoul (KR); Jung-Hoon Park, Suwon-si (KR); Jae-Won Moon, Bucheon-si (KR); Young-Ho Ha, Daegu (KR); Cheol-Hee Lee, Andong-si (KR); Chang-Hwan Son, Daegu (KR); Jong-Man Kim, Ansan-si (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 1525 days.

(21) Appl. No.: 11/697,318

(22) Filed: Apr. 6, 2007

(65) Prior Publication Data

US 2007/0236656 A1    Oct. 11, 2007

(30) Foreign Application Priority Data

Apr. 6, 2006  (KR) .................. 10-2006-0031426

(51) Int. Cl.
*G02B 26/08*  (2006.01)
*G02B 26/10*  (2006.01)
*G02B 26/12*  (2006.01)
*G02B 26/00*  (2006.01)
*G02F 1/29*   (2006.01)

(52) U.S. Cl. ..................................... 359/222.1; 359/237
(58) Field of Classification Search ................. 351/218, 351/222, 223, 245, 246
See application file for complete search history.

(56) References Cited

U.S. PATENT DOCUMENTS

| | | | | |
|---|---|---|---|---|
| 7,032,821 | B2* | 4/2006 | McClure et al. | 235/386 |
| 7,145,571 | B2* | 12/2006 | Jones et al. | 345/589 |
| 7,502,032 | B2* | 3/2009 | Richardson et al. | 345/591 |
| 7,605,930 | B2* | 10/2009 | Suzuki et al. | 358/1.14 |
| 2005/0134800 | A1* | 6/2005 | Kim | 351/242 |

FOREIGN PATENT DOCUMENTS

| | | |
|---|---|---|
| KR | 1999-65548 | 8/1999 |
| KR | 2005-44114 | 5/2005 |

* cited by examiner

*Primary Examiner* — Joseph P Martinez
*Assistant Examiner* — Brandi Thomas
(74) *Attorney, Agent, or Firm* — Cha & Reiter, LLC

(57) ABSTRACT

Disclosed is a method for evaluating the qualities of the user's color vision by means of the FM chromaticity test or directly measuring the defective factors of the user causing the color blindness. Thus it modifies the color composition of a video displaying apparatus according to a numerical analysis of the color and degree of color blindness specific to each dichromatic individual, so that he may perceive the same colors as the normal person. Also discloses is an apparatus for performing the method steps described herein.

22 Claims, 3 Drawing Sheets

METHOD OF MODIFYING COLOR COMPOSITION FOR A COLOR-BLIND PERSON IN A MOBILE DISPLAYING APPARATUS

CLAIM OF PRIORITY

This application claims, the benefit of the earlier filing date under 35 U.S.C. §119, to that patent application entitled "Method of Modifying Color Composition for a Color-Blind Person in a Mobile Displaying Apparatus," filed in the Korean Intellectual Property Office on Apr. 6, 2006 and assigned Serial No. 2006-31426, the contents of which are incorporated herein by reference.

BACKGROUND OF THE INVENTION

1. Field of the Invention

The present invention relates to a method of modifying color composition for a color-blind person in a mobile displaying apparatus, and more particularly a method of enabling a mobile displaying apparatus to generate color composition modified for a color-blind person to perceive the same color as a person with the normal color vision.

2. Description of the Related Art

Generally people's color vision for perceiving colors through the light-sensitive receptor cells differs from each other so that they perceive one and the same color differently from each other. The color-blind person particularly has an anomaly of color vision compared to the normal person.

Color blindness is defect of vision affecting the ability to distinguish colors. Color blindness is usually classified into achromatopsia and dichromatism, respectively, which provide a measure of the levels of color blindness; total or the partial color blindness, respectively. The vision mainly concerned with the color, form, distance, and tridimensional extension of objects begins with the impact of light waves on the light-sensitive receptor cells of the retina of the eye. The light-sensitive receptor cells consist of conical photosensitive receptor cells, called cones, functioning in color vision and rod-shaped photosensitive receptor cells, called rods, that are responsive to faint light. The cones also consist of three kinds of cells represented by L (Red), M (Green) and S (Blue), respectively, which are responsive to light waves. The color-blind person has one or more of these three kinds affected so as to prevent normal collecting of color information. The most common dichromatic form of color-blindness, (partial color-blind) has a malfunctioning of the L or M cells so that there is an inability to differentiate between the reds and the greens or to perceive either reds or greens. This phenomenon is shown by the characteristic spectral curve of the cones deviated from the normal region.

Hence, the weak color vision of the dichromatic person must be supplemented by augmenting the stimulation of the cones compared to that of the normal person in order to effectively distinguish colors. An example of this is disclosed in Korean Laid-Open Patent Publication No. 2005-0044114 entitled as "Method and Apparatus for Modifying Color Composition of a Video Display by Considering the Qualities of the Color Vision of a Dichromatic Person".

FIG. 1 is a flowchart for illustrating the conventional process of modifying color composition of a video display according to the result of evaluating the qualities of the color vision of a user. Referring to FIG. 1, when starting to watch a TV, the user firstly displays a test pattern for color blindness retrieved from a memory in order test the qualities of his color vision in step S10. In this case, the test is performed by using the conventional color blindness test pattern, to which the user responds by operating the input keys of a TV remote control to enter the test result to evaluate his color vision qualities in step S20. If the test result indicates color blindness, its type is also evaluated. If the test result indicates the normal color vision, the gains of the original RGB signals are not modified in step S21, or else the gains must be modified.

If the user is evaluated to have the first-type dichromatism in step S30, the gains of the original G and B signals are reduced to 0.75 times their original values in step S31 because the first-type dichromatism shows the "R" sensitivity reduced to 0.75 times the normal sensitivity. In this case, the modification of the RGB gains is carried out by adjusting the contrast gains, and therefore the gains are normalized to "1" at maximum. This process is also applied to the other types of dichromatism.

Alternatively, if the user is evaluated to have the second-type dichromatism in step S40, the gains of the original R and B signals are reduced to 0.7 times their original values in step S41 because the second-type dichromatism shows the "G" sensitivity reduced to 0.7 times the normal sensitivity. Finally, if the user is evaluated to have the third-type dichromatism in step S50, the gains of the original R and G signals are reduced to 0.5 times their original values in step S50 because the third-type dichromatism shows the "B" sensitivity reduced to 0.5 times the normal sensitivity.

However, such conventional method cannot modify the color composition of a video display so as to fit each individual's color vision differing in the color and degree of color blindness since it employs the fixed gains predetermined for each of the three types of dichromatism.

SUMMARY OF THE INVENTION

The present invention provides a method of modifying the color composition of a video displaying apparatus according to a numerical analysis of the color and degree of color blindness specific to each dichromatic individual, so that that person may perceive the same colors as the normal person.

According to an aspect of the present invention, a method of modifying color composition for a color-blind person in a mobile displaying apparatus comprises the steps of causing the mobile displaying apparatus to evaluate the qualities of the user's color vision when the user does not have this information, and modifying the color composition according to the qualities.

According to another aspect of the present invention, a method of modifying color composition for a color-blind person in a mobile displaying apparatus, comprises the steps of causing the user to select achromatopsia or dichromatism when he has the information of the qualities of his color vision, formulating the degree of dichromatism into a mathematical formula when the user selects dichromatism, and modifying the color composition according to the degree of the dichromatism formulated.

BRIEF DESCRIPTION OF THE DRAWINGS

The above features and advantages of the present invention will become more apparent from the following detailed description when taken in conjunction with the accompanying drawing in which.

DETAILED DESCRIPTION

Figure 1:
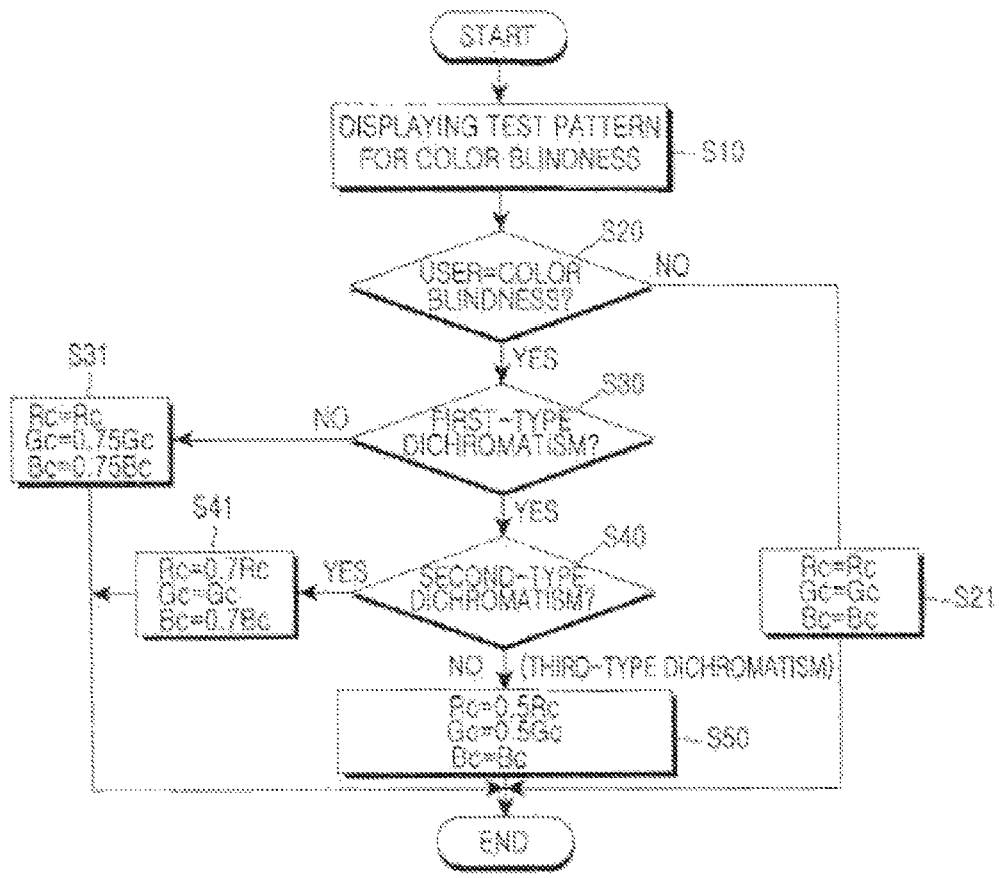
FIG. 1 is a flowchart for illustrating the conventional process of modifying the color composition of a video display according to the user's color vision qualities tested.

Exemplary embodiments of the present invention will be described herein below with reference to the accompanying drawings. In the drawings, the same or similar elements are denoted by the same reference numerals even though they are depicted in different drawings. For the purposes of clarity and simplicity, well-known functions or constructions are not described in detail since they would obscure the invention in unnecessary detail.

Referring to the population statistics, it is considered that color blindness has affected about 5.9% of men and 0.44% of women. The color blindness is also divided into total color blindness, achromatopsia or monochromatism, causing all hues to be perceived as variations of gray and partial color blindness, dichromatism, causing the inability to differentiate between reds and greens or to perceive either reds or greens. The partial color blindness may also be divided into the three-color anomaly—complete inability to perceive a particular color—and the two-color anomaly—complete inability to perceive a particular color. The statistics also has shown that the number of the persons with the three-color anomaly doubles that of the persons with the two-color anomaly. It has also shown that about 0.0001% of the persons with the partial color blindness can hardly distinguish blue. The number of the persons affected by achromatopsia or monochromatism occupies about 0.003%. Color blindness still remains incurable, and therefore the persons affected by it need specially prepared lenses in order to perceive the natural colors.

The present invention provides a color modifying program to modify the color information of a multimedia content according to the qualities of the user's color vision and environmental factors, which enables a color-blind person to almost correctly perceive the colors of the multimedia content displayed in a TV, computer, PDA, mobile phone, etc. This is achieved by modifying the original color composition of a video display so as to compensate for the defective visual qualities of a color-blind person.

A mobile displaying apparatus used for the inventive method includes a key input part for inputting data such as phone numbers or various commands for testing the qualities of the user's color vision, a storage device for storing a test program used for evaluating the qualities of the user's color vision by means of Farnsworth-Munsell (FM) chromaticity test or directly measuring the defective factors of the user causing the color blindness under the control of a control unit, a test analyzer for analyzing the qualities of the user's color vision according to the test program, and a display for displaying image or multimedia data, wherein the control unit controls the whole functions of the displaying apparatus and evaluates the qualities of the user's color vision based on the results of executing the test program so as to modify the original color composition of the display. The display is an LCD (Liquid Crystal Display) for composing natural colors by means of three primary colors of red, green and blue.

Figure 2:
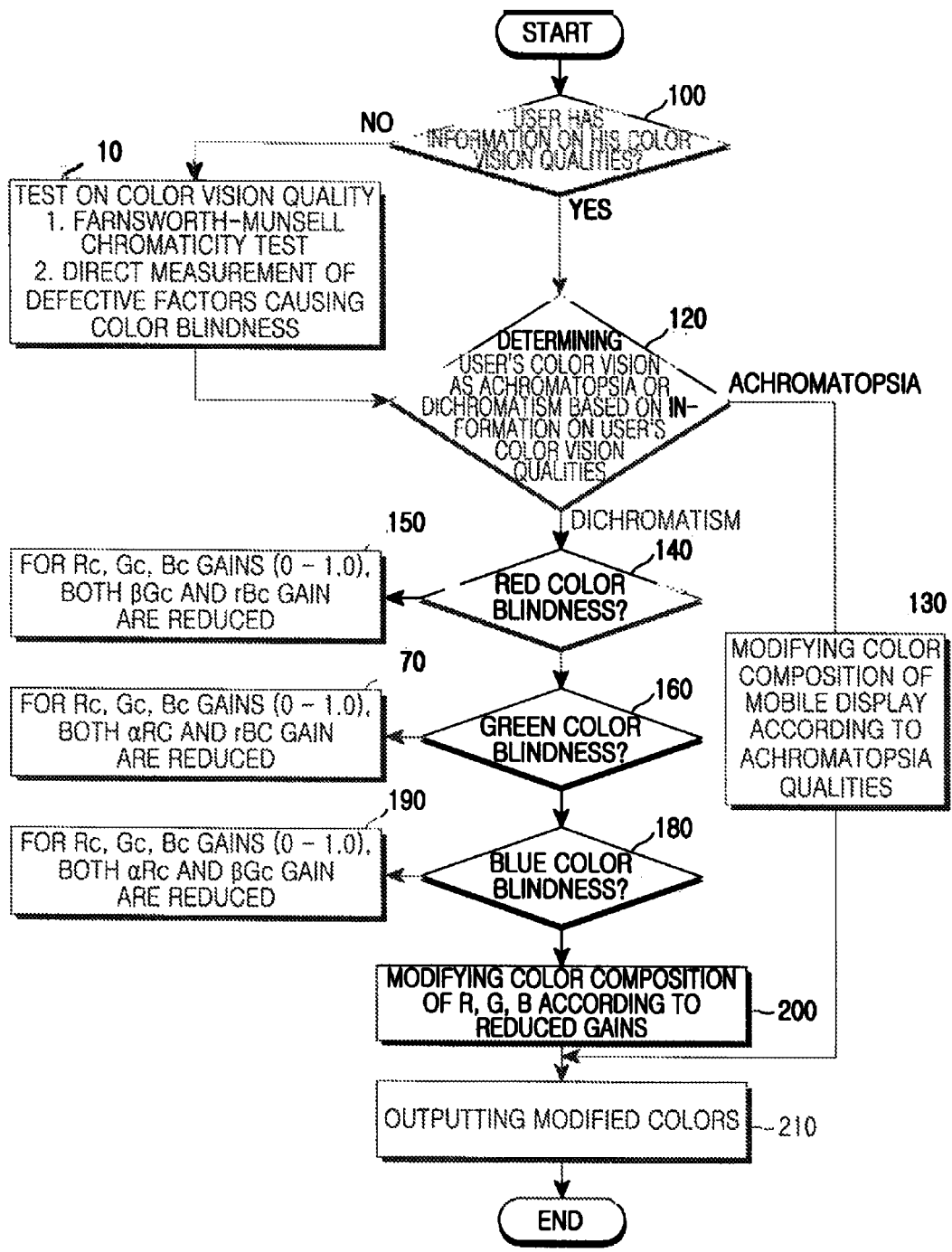
FIG. 2 is a flowchart for illustrating a method of modifying the color composition of a mobile displaying apparatus for a color-blind person according to the present invention.

Referring to the flowchart of FIG. 2, the inventive method of modifying the color composition of the display so as to compensate color blindness starts with confirming in step 100 that the user has the information on his color vision qualities.

If not having it, he selects from a menu displayed the operation for testing his color vision qualities by operating the key input part in step 110. Accordingly the control unit controls the test analyzer so as to display varieties of testing method. But if he has the information, he selects achromatopsia or dichromatism by operating the key input part.

The test program stored in the storage device includes two kinds of the processes to test the qualities of the user's color vision. The first process is a direct measurement of the defective factors of the user causing the color blindness that is to calculate both deviation and sensitivity of the defective cones causing color blindness, and to combine the two values so as to obtain both the kind of color blindness (red blindness, green blindness, blue blindness) and its defective degree.

The second process is to employ the result of testing the qualities of the user's color vision. This is generally done by employing the pseudoisochromatic table or color arrangement test. A typical example of employing the pseudoisochromatic table is the Ishihara Test. Although the Ishihara Test is most widely used for easiness and speediness of testing, it does not satisfy the precision of measurement of the color vision qualities. On the contrary, the color arrangement test is advantageous in measuring exactly both kind and degree of the color vision qualities. The inventive method employs the FM chromaticity test to determine the user's color vision as achromatopsia or dichromatism based on the total error score (TES) obtained.

After testing the qualities of the user's color vision by employing the test process chosen by the user, the control unit determines the user's color vision as achromatopsia or dichromatism in step 120. If the user has achromatopsia, the control unit modifies the color composition of the display according to the qualities of the user's achromatopsia in step 130. Hereinafter, the primary colors of red, green and blue used in the display are simply represented by "R", "G" and "B", which are more specifically defined as $R_c$, $G_c$, $B_c$. The control unit formulates the degree of color blindness as expressed by the following:

$$R_C = \alpha R_C$$

$$G_C = \beta G_C$$

$$B_C = \gamma B_C$$

Wherein $\alpha$, $\beta$, $\gamma$ are constants respectively representing the degrees of red, green and blue color blindness. Namely, red color blindness is represented by $\alpha=1$, green color blindness by $\beta=1$, and blue color blindness by $\gamma=1$.

Figure 3:
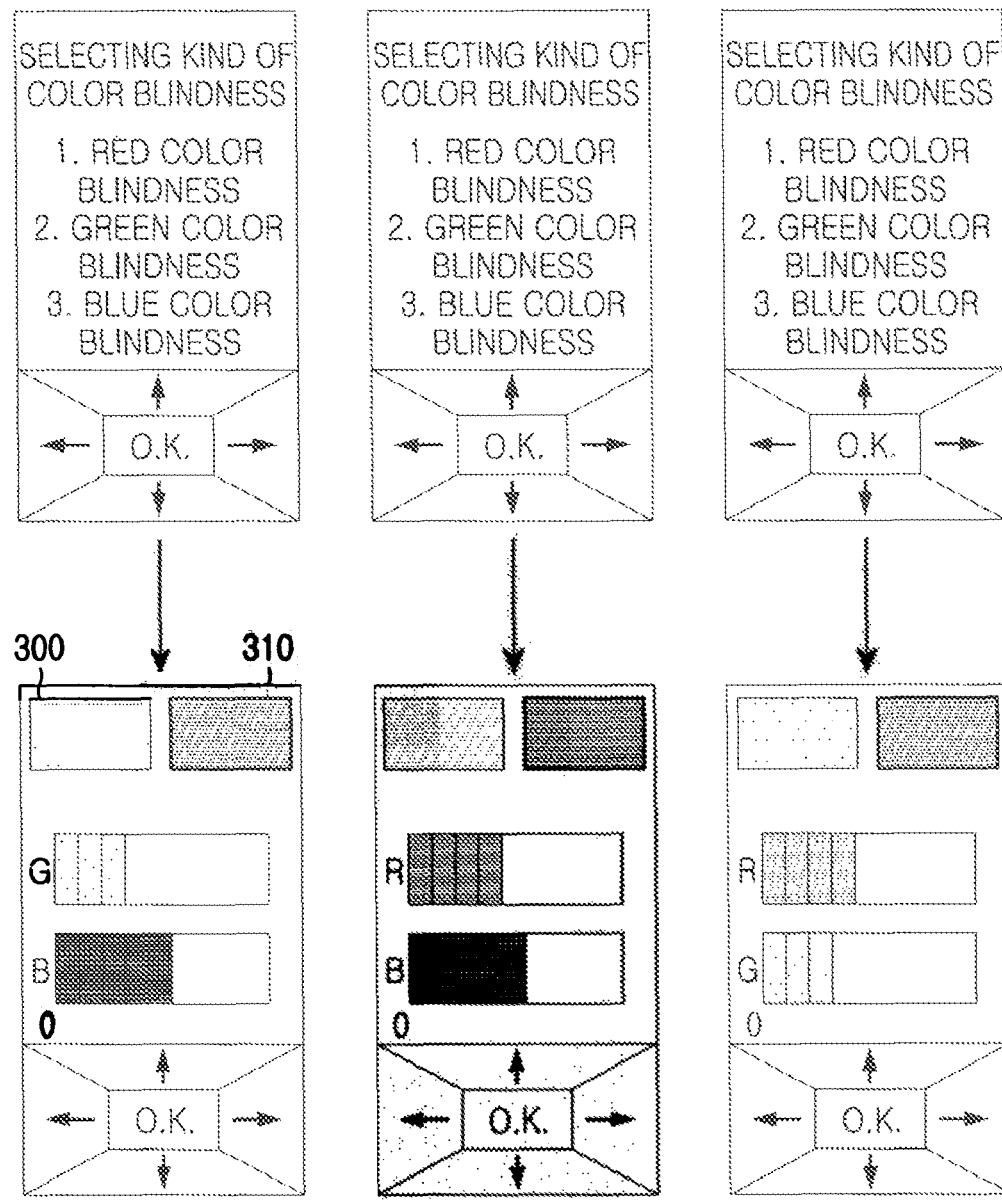
FIG. 3 is an example of a menu displaying the types of dichromatism and the gain adjustment of the RGB channels in a mobile displaying apparatus according to the present invention.

Referring to FIG. 3 for illustrating a menu displaying the kinds of color blindness and the gain adjustments of the RGB channels, the user selects a kind of color blindness by operating the key input part in order to formulate the degree of his color blindness. Then the control unit displays a menu representing the patches and gain adjustments of the RGB channels. In this case, the control unit formulates the degree of color blindness by adjusting the RGB gain from 0 to 1.0 so as to fit the hue and degree of color blindness specific to each individual.

If the user is determined as having red color blindness in step 140, the control unit adjusts in step 150 the adjustment patch 310 up to gray compared to the reference patch 300 and reduces the gains of both G and B according to the degree of the red color blindness. Namely, $R_C = \alpha R_C$ is adjusted to $\alpha=1$, and the G and B gains respectively to $G_C = 0.3 G_C$ and $B_C = 0.5 B_C$.

Subsequently, the control unit modifies in step 200 the color composition of the display according to the reduced G and B gains, thus displaying data such as characters, image and multimedia content with the colors fitting the qualities of the user's color blindness.

Alternatively, if the user is determined as having green color blindness in step 160, the control unit adjusts in step 170 the adjustment patch 310 up to gray compared to the reference patch 300 and reduces the gains of both R and B according to the degree of the green color blindness. Namely, $G_C=\beta G_C$ is adjusted to $\beta=1$, and the R and B gains respectively to $R_C=0.4R_C$ and $B_C=0/5B_C$.

Subsequently, the control unit modifies in step 200 the color composition of the display according to the reduced R and B gains, thus displaying data such as characters, image and multimedia content with the colors fitting the qualities of the user's color blindness.

Alternatively, if the user is determined as having blue color blindness in step 180, the control unit adjusts in step 190 the adjustment patch 310 up to gray compared to the reference patch 300 and reduces the gains of both R and G according to the degree of the blue color blindness. Namely, $B_C=\gamma B_C$ is adjusted to $\gamma=1$, and the R and G gains respectively to $R_C=0.4R_C$ and $G_C=0.3G_C$.

Subsequently, the control unit modifies in step 200 the color composition of the display according to the reduced R and G gains, thus displaying data such as characters, image and multimedia content with the colors fitting the qualities of the user's color blindness in step 210.

As described above, the inventive method evaluates the qualities of the user's color vision by means of the FM chromaticity test or directly measuring the defective factors of the user causing the color blindness. Thus it modifies the color composition of a video displaying apparatus according to a numerical analysis of the color and degree of color blindness specific to each dichromatic individual, so that he may perceive the same colors as the normal person.

The above-described method according to the present invention can be realized as software and can be stored in a recording medium such as a CD ROM, a RAM, a floppy disk, a hard disk or a magneto-optical disk, so that a user can read such software by using a computer or processor. Or the software may be downloaded over a network. When the software is downloaded into a memory accessible by the processor or computer chip, the processor or computer chip operates as an apparatus to execute the processing steps illustrated herein.

While the invention has been shown and described with reference to a certain preferred embodiment thereof, it will be understood by those skilled in the art that various changes in form and details may be made therein without departing from the spirit and scope of the invention.

What is claimed is:

1. A method of modifying color composition for a color-blind person in a mobile displaying apparatus containing a processor and a memory, the method comprising the steps of:
   causing a processor of said mobile displaying apparatus to evaluate the qualities of a particular user's color vision when the particular user does not provide information about said qualities employing by the processor of said mobile display apparatus a Farnsworth-Munsell (FM) chromaticity test for both achromatopsia and dichromatism and according to a total error scored (TES) of the FM chromaticity test, determining whether the user's color-blindness is achromatopsia or dichromatism; and
   modifying said color composition according to said qualities specific to the particular user, in which the color composition is modified over a range of 0 to 1.0 so the mobile displaying apparatus provides color composition based on a severity and classification of color-blindness customized for the particular user, in which the modified color composition is provided by the display apparatus for one of dichromatism and achromatopsia in accordance with a respective determining of the user's color-blindness by the FM chromaticity test.

2. The method as defined in claim 1, wherein the step of evaluating said qualities further comprises directly measuring the defective factors of the user causing the color blindness.

3. The method as defined in claim 1, including the step of formulating the degree of the color blindness as expressed by the following Formula 1 when the user is evaluated to be color-blind:

$$R_C=\alpha R_C$$
$$G_C=\beta G_C$$
$$B_C=\gamma B_C \hspace{2cm} \text{Formula 1.}$$

4. The method as defined in claim 3, wherein the color blindness is classified into red-dichromatism, green-dichromatism and blue-dichromatism.

5. The method as defined in claim 3, wherein the step of formulating the degree of the color blindness is to reduce both the green gain $\beta$ and the blue gain $\gamma$ when the user is of red-dichromatism.

6. The method as defined in claim 5, wherein the color composition of green and blue are modified according to the reduced values of the green and the blue gain $\beta$ and $\gamma$.

7. The method as defined in claim 3, wherein the step of formulating the degree of the color blindness is to reduce both the red gain $\alpha$ and the blue gain $\gamma$ when the user is of green-dichromatism.

8. The method as defined in claim 7, wherein the color composition of red and blue are modified according to the reduced values of the green and the blue gain $\alpha$ and $\gamma$.

9. The method as defined in claim 3, wherein the step of formulating the degree of the color blindness is to reduce both the red gain $\alpha$ and the green gain $\beta$ when the user is of blue-dichromatism.

10. The method as defined in claim 9, wherein the color composition of red and green are modified according to the reduced values of the red and the green gain $\alpha$ and $\beta$.

11. The method as defined in claim 2, wherein the color composition is modified to fit achromatopsia when the user is evaluated to be achromatopsia.

12. A method of modifying color composition for a color-blind person in a mobile displaying apparatus containing a processor in communication with a memory, the method comprising the steps of:
   prompting by a control unit of the mobile display apparatus to the user to select achromatopsia or dichromatism when said user has the information of the qualities of his color vision;
   formulating a degree of dichromatism into a mathematical formula when the user selects dichromatism; and
   modifying said color composition according to the degree of the dichromatism formulated specific to the particular user, in which the color composition is modified over a range of 0 to 1.0 so the mobile displaying apparatus provides color composition based on a severity and classification of color-blindness customized for the particular user,
   wherein a test program comprises employing by the processor of said mobile display apparatus a Farnsworth-Munsell (FM) chromaticity test for both achromatopsia and dichromatism, and according to a total error scored (TES) of the FM chromaticity test, determining whether the user's color-blindness is achromatopsia or dichromatism;

and wherein color composition modification is provided by the display apparatus for one of dichromatism and achromatopsia in accordance with a respective determining of the user's color-blindness by the FM chromaticity test.

13. The method as defined in claim 12, wherein the step of formulating the degree of the color blindness is to reduce both the green gain β and the blue gain γ when the user is of red-dichromatism.

14. The method as defined in claim 13, wherein the color composition of green and blue are modified according to the reduced values of the green and the blue gain β and γ.

15. The method as defined in claim 12, wherein the step of formulating the degree of the color blindness is to reduce both the red gain α and the blue gain γ when the user is of green-dichromatism.

16. The method as defined in claim 15, wherein the color composition of red and blue are modified according to the reduced values of the green and the blue gain α and γ.

17. The method as defined in claim 12, wherein the step of formulating the degree of the color blindness is to reduce both the red gain α and the green gain β when the user is of blue-dichromatism.

18. The method as defined in claim 17, wherein the color composition of red and green are modified according to the reduced values of the red and the green gain α and β.

19. The method as defined in claim 12, wherein the color composition is modified so as to fit achromatopsia when the user selects achromatopsia.

20. An apparatus for adjusting the color composition in a portable device, the apparatus comprising;

a processor in communication with a memory, the processor executing code for executing the steps of:

displaying a pattern to evaluate qualities of a particular user's color vision when the does not provide information about said qualities; and modifying said color composition according to said qualities specific to the particular user, in which the color composition is modified over a range of 0 to 1.0 so the mobile displaying apparatus provides color composition based on a severity and classification of color-blindness customized for the particular user, by individually adjusting the levels of red, green and blue hues by at least one known factor; and employing by the processor of said mobile display apparatus a Farnsworth-Munsell (FM) chromaticity test for both achromatopsia and dichromatism and according to a total error scored (TES) of the FM chromaticity test, determining whether the user's color-blindness is achromatopsia or dichromatism.

21. The apparatus as recited in claim 20, further comprising:

means for inputting values for evaluating the qualities of the user's color vision.

22. The apparatus as recited in claim 21, wherein the processor further executing the steps of:

responsive to the users inputs, adjusting the color composition by adjusting the gains of red, green, blue color.

* * * * *

UNITED STATES PATENT AND TRADEMARK OFFICE
CERTIFICATE OF CORRECTION

PATENT NO. : 8,345,338 B2
APPLICATION NO. : 11/697318
DATED : January 1, 2013
INVENTOR(S) : Young-Min Jeong et al.

It is certified that error appears in the above-identified patent and that said Letters Patent is hereby corrected as shown below:

In the Claims:

Column 8, Claim 20, Line 6 should read as follows:
--...vision when the particular user does not provide...--

Signed and Sealed this
Twenty-third Day of April, 2013

Teresa Stanek Rea
*Acting Director of the United States Patent and Trademark Office*